(12) United States Patent
Ohya et al.

(10) Patent No.: US 11,001,691 B2
(45) Date of Patent: May 11, 2021

(54) POROUS POLYETHER SULFONE FILM AND PRODUCTION METHOD THEREFOR

(71) Applicant: UBE INDUSTRIES, LTD., Yamaguchi (JP)

(72) Inventors: Shusei Ohya, Yamaguchi (JP); Makoto Matsuo, Yamaguchi (JP); Keita Bamba, Yamaguchi (JP)

(73) Assignee: UBE INDUSTRIES, LTD., Yamaguchi (JP)

( * ) Notice: Subject to any disclaimer, the term of this patent is extended or adjusted under 35 U.S.C. 154(b) by 124 days.

(21) Appl. No.: 16/320,418

(22) PCT Filed: Jul. 25, 2017

(86) PCT No.: PCT/JP2017/026910
§ 371 (c)(1),
(2) Date: Jan. 24, 2019

(87) PCT Pub. No.: WO2018/021337
PCT Pub. Date: Feb. 1, 2018

(65) Prior Publication Data
US 2019/0276628 A1    Sep. 12, 2019

(30) Foreign Application Priority Data

Jul. 25, 2016  (JP)  ............... JP2016-145753

(51) Int. Cl.
*C08J 9/26* (2006.01)
*B01D 67/00* (2006.01)
(Continued)

(52) U.S. Cl.
CPC ............... *C08J 9/26* (2013.01); *B01D 39/16* (2013.01); *B01D 67/0016* (2013.01);
(Continued)

(58) Field of Classification Search
CPC .......................................................... C08J 9/26
(Continued)

(56) References Cited

U.S. PATENT DOCUMENTS 5,869,174 A    2/1999  Wang
6,284,137 B1   9/2001  Hajikano et al.
(Continued)

FOREIGN PATENT DOCUMENTS

JP    60-41503 A     3/1985
JP    2001-509431 A  7/2001
(Continued)

OTHER PUBLICATIONS

International Search Report dated Oct. 31, 2017 corresponding to International Patent Application No. PCT/JP/2017/026910, filed on Jul. 25, 2017; 2 pages.
(Continued)

*Primary Examiner* — Brent T O'Hern
(74) *Attorney, Agent, or Firm* — Mintz Levin Cohn Ferris Glovsky and Popeo PC

(57) ABSTRACT

Provided are: a porous polyether sulfone film having macrovoids and having excellent dimensional stability; and a production method therefor. Provided is a porous polyether sulfone film having a surface layer (a), a surface layer (b), and a macrovoid layer interposed between the surface layer (a) and the surface layer (b). The macrovoid layer has a partition wall joined to the surface layers (a) and (b) and a plurality of macrovoids surrounded by the partition wall and the surface layers (a) and (b). The surface layer (a) and the surface layer (b) have pores connected to the macrovoids.

11 Claims, 2 Drawing Sheets

(51) Int. Cl.
  *B01D 69/02* (2006.01)
  *B01D 71/68* (2006.01)
  *C12N 5/00* (2006.01)
  *F16L 59/02* (2006.01)
  *B01D 39/16* (2006.01)

(52) U.S. Cl.
  CPC ......... *B01D 67/0083* (2013.01); *B01D 69/02* (2013.01); *B01D 71/68* (2013.01); *C12N 5/0068* (2013.01); *F16L 59/028* (2013.01); *F16L 59/029* (2013.01); *B01D 2323/22* (2013.01); *B01D 2325/02* (2013.01); *B01D 2325/04* (2013.01); *C08J 2381/06* (2013.01); *C12N 2533/30* (2013.01)

(58) Field of Classification Search
  USPC .......................................................... 428/215
  See application file for complete search history.

(56) References Cited

U.S. PATENT DOCUMENTS

| | | | |
|---|---|---|---|
| 2010/0108599 A1* | 5/2010 | Vizvardi | B01D 67/0013 210/500.23 |
| 2013/0256229 A1 | 10/2013 | Wang et al. | |
| 2015/0306539 A1 | 10/2015 | Yamato | |

FOREIGN PATENT DOCUMENTS

| | | |
|---|---|---|
| JP | 2001-515396 A | 9/2001 |
| JP | 2008-6327 A | 1/2008 |
| JP | 2010-513021 A | 4/2010 |
| JP | 2014-231572 A | 12/2014 |
| JP | 2016-106022 A | 6/2016 |
| WO | 95/33549 A1 | 12/1995 |
| WO | 96/40421 A1 | 12/1996 |
| WO | 99/02248 A1 | 1/1999 |
| WO | 2008/076599 A1 | 6/2008 |

OTHER PUBLICATIONS

International Preliminary Report on Patentability dated Jan. 29, 2019 corresponding to International Patent Application No. PCT/JP/2017/026910, filed on Jul. 25, 2017; 5 pages.

European First Examination Report dated Aug 26, 2020 corresponding to EP 17 834 339.8; 3 pages.

Flory-Huggins Parameter; Polymer Properties Database © 2015-2020 polymerdatabase.com; https://polymerdatabase.com/polymer%physics/Excluded%20Volume2.html downloaded Oct 20, 2020; 3 pages.

* cited by examiner (B)

(A)

(C)

POROUS POLYETHER SULFONE FILM AND PRODUCTION METHOD THEREFOR

FIELD

The present invention relates to a porous polyethersulfone film and a method for manufacturing the same.

BACKGROUND

Conventionally, a porous polysulfone film is widely used in applications including material separation (for example, a liquid filtering membrane and a gas separation membrane, etc.). PTL 1 describes a porous film made of polysulfone, which: is composed of a mixed polymer of polyarylsulfone and polyethersulfone at a weight ratio of 9/1 to 1/9; is an inclined-type porous film wherein many micropores communicate from one surface to the other surface of the film, so as to form a mesh polymer network structure; is composed of two layers, specifically a dense layer having many pores with pore diameters ranging from 0.01 μm to 1 μm and separation functions, and an inclined-type support layer that supports the dense layer and has pore diameter distribution wherein pores existing therewithin have diameters ranging from 1 μm to 100 μm and the pore diameter successively increases from the dense layer side to the other surface side; and has a fraction particle diameter of 0.5 μm or less.

PTL 2 describes a hollow-fiber porous film, which is formed of a film-forming solution containing 10% by mass to 40% by mass of a polymer component selected from polysulfone and polyethersulfone, 20% by mass to 60% by mass of a good solvent selected from N-methyl-2-pyrrolidone, dimethyl sulfoxide, dimethylacetamide, and dimethylformamide, 10% by mass to 60% by mass of a poor solvent selected from glycols, and 1% by mass to 25% by mass of polyvinyl pyrrolidone.

PRIOR ART DOCUMENTS

Patent Literatures

PTL 1: WO95/33549
PTL 2: JP2008-6327A

DISCLOSURE OF THE INVENTION

Problems to be Solved by the Invention

Polyethersulfone is excellent in dimensional stability, and thus is useful for production of a porous film having a controlled pore diameter. However, a porous polyethersulfone film having macrovoids has not been obtained by conventional techniques. An object of the present invention is to provide a porous polyethersulfone film having macrovoids and excellent dimensional stability and a method for manufacturing the same.

Means for Solving the Problems

The present invention provides the following porous polyethersulfone film the method for manufacturing the same.

[1]
A porous polyethersulfone film having a surface layer (a), a surface layer (b), and a macrovoid layer sandwiched between the surface layer (a) and the surface layer (b), wherein the macrovoid layer has a partition wall bonded to the surface layers (a) and (b); and a plurality of macrovoids surrounded by the partition wall and the surface layers (a) and (b), the macrovoids having an average pore diameter in the film plane direction of 10 μm to 500 μm;
wherein the partition wall of the macrovoid layer has a thickness of 0.1 μm to 50 μm;
wherein each of the surface layers (a) and (b) has a thickness of 0.1 μm to 50 μm;
wherein one of the surface layers (a) and (b) has a plurality of fine pores having an average pore diameter of more than 5 μm and not more than 200 μm, while the other has a plurality of fine pores having an average pore diameter of not less than 0.01 μm and not more than 200 μm;
wherein a surface opening ratio of one of the surface layers (a) and the surface layer (b) is not less than 15%, while the surface opening ratio of the other surface layer is not less than 10%;
wherein the fine pores in the surface layers (a) and (b) communicate with the macrovoid; and
wherein the porous polyethersulfone film has a total film thickness of 5 μm to 500 μm, and a porosity of 50% to 95%.

[2]
The porous polyethersulfone film according to [1], wherein a mean flow pore diameter measured by a palm porometer is 5 to 200 μm.

[3]
The porous polyethersulfone film according to [1] or [2], wherein the partition wall of the macrovoid layer, and the surface layers (a) and (b) have generally the same thickness.

[4]
The porous polyethersulfone film according to any one of [1] to [3], wherein the Gurley value is not more than 20 secs.

[5]
The porous polyethersulfone film according to any one of [1] to [4], wherein in the cross section of the porous polyethersulfone film cut perpendicularly to the film plane direction, a cross-sectional area of the macrovoid having an average pore diameter in the film plane direction of 10 μm to 500 μm is not less than 50% of a film cross-sectional area.

[6]
The porous polyethersulfone film according to any one of [1] to [5], wherein in the cross section of the porous polyethersulfone film cut perpendicularly to the film plane direction, not less than 60% of the total number of the macrovoids has a ratio (L/d) of 0.5 to 3 of a length (L) in the film plane direction to a length (d) in the film thickness direction.

[7]
The porous polyethersulfone film according to any one of [1] to [6], wherein the glass transition temperature of the porous polyethersulfone film is 200° C. or higher, or a clear transition temperature of the porous polyethersulfone film is not observed.

[8]
The method for manufacturing a porous polyethersulfone film according to any one of [1] to [7], the method comprising the steps of:
casting a polyethersulfone solution (A) containing 0.3% by mass to 60% by mass of a polyethersulfone having a logarithmic viscosity of 0.5 to 1.0, and 40% by mass to 99.7% by mass of an organic polar solvent in a film shape, and dipping or bringing into contact with a coagulating solvent containing a poor solvent or non-solvent of polyethersulfone as an essential component to fabricate a coagulated film having a vacancy; and heat treating the coagulated film having a vacancy obtained in the step to coarsen the vacancy to obtain a porous polyethersulfone film;

wherein the heat treatment comprises heating up the coagulated film having the vacancy to the glass transition temperature of the polyethersulfone or higher, or to 240° C. or higher.

[9]

The method for manufacturing a porous polyethersulfone film according to [8], wherein the heat treatment is performed at a heating rate of 10° C./min or higher in a temperature region of 80° C. or higher.

[10]

The method for manufacturing a porous polyethersulfone film according to [8] or [9], wherein the poor solvent or nonsolvent is water.

[11]

The method for manufacturing a porous polyethersulfone film according to any one of [8] to [10], wherein a ratio of water in the coagulating solvent is 20% by mass to 100% by mass.

Effects of the Invention

According to the present invention, a porous polyethersulfone film having macrovoids and excellent dimensional stability and a method for manufacturing the same are provided.

DESCRIPTION OF EMBODIMENTS

Figure 1:
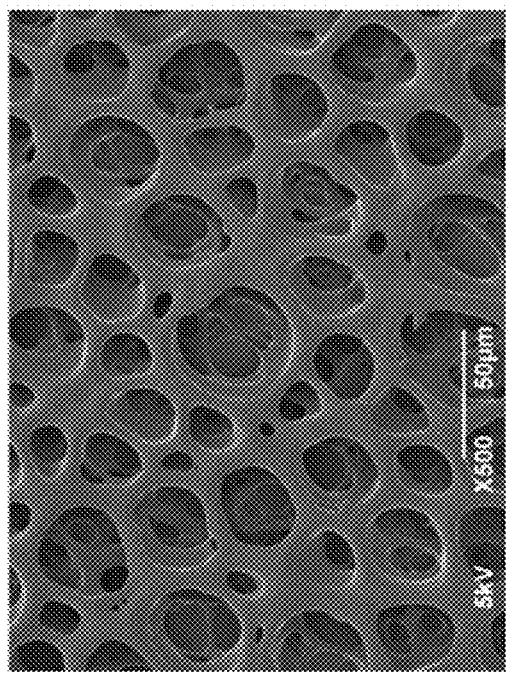
FIG. 1 illustrates scanning electron micrographs of the porous polyethersulfone film obtained in Example 2, wherein (A) depicts the surface on the side of a surface layer (a), (B) depicts the surface on the side of a surface layer (b), and (C) depicts a cross section (the upper side of the page denotes the side of the surface layer (a), and the lower side of the page denotes the side of the surface layer (b).).
Figure 1:
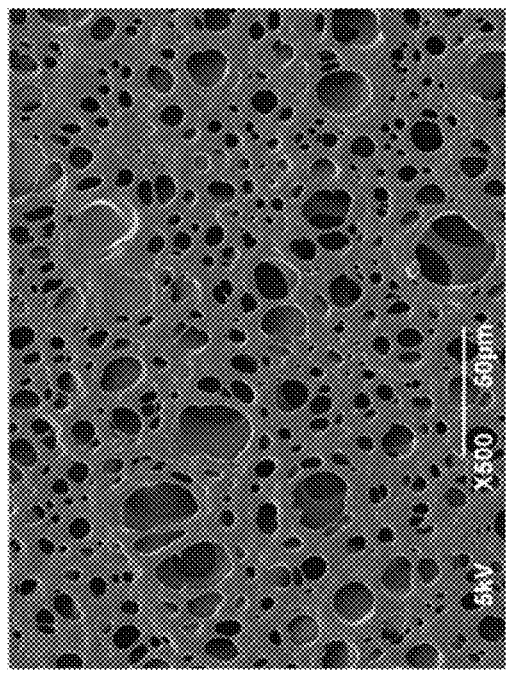
Figure 1:
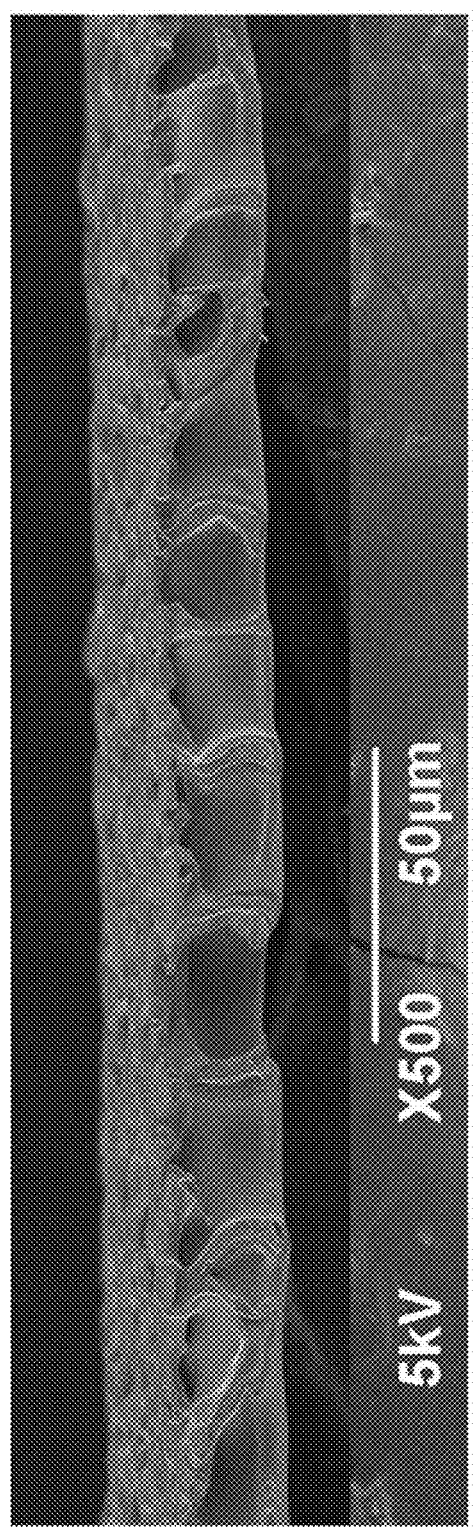

Hereafter, illustrated aspects of the present invention are described, however, the present invention is not limited to these aspects. Note that each characteristic value disclosed herein is measured by the methods described in the section of "Examples" of the present specification unless otherwise specified.

<Porous Polyethersulfone Film>

One aspect of the present invention provides a porous polyethersulfone film having surface layers (a) and (b), and a macrovoid layer sandwiched between the surface layers (a) and (b). In one typical aspect, the porous polyethersulfone film of the present invention has a three-layer structure composed of the surface layers (a) and (b), and a macrovoid layer.

The porous polyethersulfone film according to one aspect of the present invention has a specific porous structure as described later, and specifically has a film structure having macrovoids, which has never been achieved in the case of polyethersulfone films. The porous polyethersulfone film according to one aspect of the present invention has advantages such that: 1) because of a high porosity, the film has good material permeability; 2) because of having through-pores that penetrate from one surface to the other surface, filling with and movement of substances can be easily performed; and 3) because of having macrovoids, the amount of substances to be filled can be increased. Moreover, when the partition walls of macrovoids are ladder-shaped, an advantage can be obtained such that the film has proof stress against compressive stress in the film thickness direction and has particularly high dimensional stability, in spite of its relatively high strength compared to bulk density and high porosity. The porous polyethersulfone film according to one aspect of the present invention is also useful as a material separation film (for example, a liquid filtering membrane and a gas separation membrane, etc.), an insulating material, and furthermore, a cell culture sheet, or the like.

The surface layers (a) and (b) each have a thickness of 0.1 μm to 50 μm, and from the viewpoint of the strength of the polyethersulfone film, preferably 0.5 μm to 10 μm, more preferably 1 μm to 9 μm, further preferably 2 μm to 8 μm, and particularly preferably 2 μm to 7 μm. From the viewpoint of using the polyethersulfone film as various flat film materials, the surface layers (a) and (b) preferably have generally the same thickness.

The surface layers (a) and (b) each have a plurality of fine pores. Of the surface layers (a) and (b), one layer has a plurality of fine pores with an average pore diameter of higher than 5 μm and 200 μm or lower, preferably 10 μm to 100 μm, and more preferably 10 μm to 50 μm, and the other layer has a plurality of fine pores with an average pore diameter of 0.01 μm or more and 200 μm or less, preferably 0.5 μm to 100 μm, and more preferably 10 μm to 100 μm.

Of the surface layers (a) and (b), one layer has a surface opening ratio of 15% or more, and preferably 20% or more, and the other layer has a surface opening ratio of 10% or more, and preferably 15% or more. Such surface opening ratios are advantageous in that material transfer between the exterior of the porous polyethersulfone film and macrovoids is improved.

Furthermore, fine pores have a maximum pore diameter of preferably 500 μm or less, and more preferably 200 μm to 100 μm, and further preferably 100 μm to 50 μm.

The fine pores in the surface layers (a) and (b) communicate with macrovoids. Accordingly, the fine pores enable good material transfer between the exterior of the porous polyethersulfone film and macrovoids, and particularly can express an advantage of allowing the penetration of a large flow of gas or liquid without a significant pressure loss.

As described above, the porous polyethersulfone film of the present invention has through-pores that penetrate from one surface to the other surface, so as to facilitate filling with and moving of substances, and be excellent in material permeability such as air permeability. In the meantime, the average pore diameter of fine pores formed on the film surface is controlled, so that the porous polyethersulfone film of the present invention has filtering functions such that the film can allow the passage of only substances of predetermined sizes.

The macrovoid layer has a plurality of macrovoids and partition walls for separating macrovoids from each other. Macrovoids are spaces surrounded by partition walls and the surface layers (a) and (b). Typically, macrovoids communicate with both surface layers (a) and (b). An average pore diameter in the film plane direction ranges from 10 μm to 500 μm, preferably 10 μm to 100 μm, and more preferably 10 μm to 80 μm.

A cross section when the macrovoid layer is cut in parallel to the film plane direction may be a honeycomb structure or a structure analogous thereto. Furthermore, a plurality of macrovoids having predetermined pore diameters are present closely to each other with partition walls between them. Specifically, the porous polyethersulfone film of the present invention may have a namely "honeycomb sandwich structure". Note that the term "honeycomb structure" as used herein merely means a structure in which many individually partitioned spaces are densely packed, and does not mean only a structure in which the spaces are precisely hexagonal.

Because of macrovoids, the porous polyethersulfone film of the present invention has large spaces and a high porosity. Accordingly, when the film is used as an insulating substrate, for example, the permittivity can be lowered, when voids are filled with a substance, for example, the amount of the substance to be filled can be increased, and when the film is used as a cell culture sheet, for example, a space for culturing cells can be increased. In this manner, various advantages can be obtained according to applications.

Partition walls for separating macrovoids from each other have a thickness of 0.1 μm to 50 μm, and from the viewpoint of the strength of the porous polyethersulfone film and communicating properties among macrovoids, preferably 1 μm to 15 μm, more preferably 2 μm to 12 μm, further preferably 3 μm to 10 μm, and particularly preferably 4 μm to 8 μm. The partition walls and the surface layers (a) and (b) preferably have generally the same thickness.

The partition walls are bonded to the surface layers (a) and (b). The partition walls have a role of separating macrovoids from each other, and a role as a support part for supporting the surface layers (a) and (b). Hence, the porous polyethersulfone film has proof stress against compressive stress in the film thickness direction regardless of its high porosity, and thus have high dimensional stability. Such an advantage is particularly significant in a cross section when the porous polyethersulfone film is cut perpendicular to the film plane direction, and when the partition walls and the surface layers (a) and (b) are composed to form a ladder shape. Note that the term "ladder-shaped (or ladder shape)" refers to a shape where the partition walls are formed almost perpendicular to the film plane direction at almost regular intervals and bonded to the surface layers (a) and (b).

From the viewpoint of material permeability, in a cross section when the porous polyethersulfone film of the present invention is cut perpendicular to the film plane direction, the cross-sectional area of macrovoids having an average pore diameter in the film plane direction of 10 μm to 500 μm accounts for, relative to the film cross-sectional area, preferably 50% or more, more preferably 60% or more, further preferably 70% or more, and particularly preferably 75% or more, and, preferably 98% or less, more preferably 95% or less, further preferably 90% or less, and particularly preferably 85% or less.

Furthermore, from the viewpoint of material permeability, lightweight property, and film structure preserving property, in a cross section when the porous polyethersulfone film of the present invention is cut perpendicular to the film plane direction, preferably 60% or more, more preferably 70% or more, further preferably 75% to 100% of the total number of macrovoids, has the ratio (L/d) of the length (L) in the film plane direction to the length (d) in the film thickness direction of preferably 0.5 to 3, more preferably L/d=0.8 to 3, further preferably L/d=1 to 3, and particularly preferably L/d=1.2 to 3. Note that the length (d) of macrovoids in the film thickness direction is the maximum length of macrovoids in the film thickness direction, and the length (L) of macrovoids in the film plane direction is the maximum length of macrovoids in the film plane direction.

The porous polyethersulfone film has a total film thickness of 5 μm to 500 μm, and from the viewpoint of mechanical strength, the thickness is preferably 10 μm or more, more preferably 20 μm or more, and further preferably 25 μm or more, and is preferably 300 μm or less, more preferably 100 μm or less, and further preferably 60 μm or less.

Furthermore, the porous polyethersulfone film has a porosity in the range of, from the viewpoint of material permeability, mechanical strength, and film structure preserving property, 50% to 95%, preferably 55% to 90%, more preferably 60% to 85%, and further preferably 60% to 80% by mass.

Furthermore, from the viewpoint of air permeability, the porous polyethersulfone film has the Gurley value (number of seconds required for 100 cc of air to pass through the film under pressure of 0.879 $g/m^2$) of preferably 20 seconds or less, more preferably 10 seconds or less, further preferably 1 second or less, and particularly preferably 0.5 second or less. The lower limit thereof is not particularly limited, but is preferably a measurement limit or higher. Gurley value can be measured in accordance with JIS P8117.

The porous polyethersulfone film has the mean flow pore diameter as measured using a palm porometer, from the viewpoint of material permeability, mechanical strength, and film structure preserving property, of preferably 5 μm to 200 nm, more preferably 10 μm to 100 nm, further preferably 10 μm to 50 nm, and particularly preferably 10 μm to 30 μm.

The porous polyethersulfone film of the present invention has a rate of change in the film thickness of, after loading with compressive stress under conditions of 200° C., 15 minutes, and 0.5 MPa, preferably 5% or less, more preferably 3% or less, and further preferably 0% to 1%. Moreover, the film has dimensional stability in the film plane direction under conditions of 200° C. and 2 hours in accordance with ASTM D1204, which is preferably within ±1% or less, more preferably within ±0.8%, and further preferably within ±0.5%.

The porous polyethersulfone film contains polyethersulfone, and typically comprises substantially polyethersulfone. Polyethersulfone may be synthesized by a method known by persons skilled in the art. For example, the film can be produced by a method that involves subjecting dihydric phenol, an alkali metal compound and a dihalogenodiphenyl compound to polycondensation reaction in an organic polar solvent, or a method that involves synthesizing in advance an alkali metal di-salt of dihydric phenol, and then subjecting the resultant to polycondensation reaction with a dihalogenodiphenyl compound in an organic polar solvent, for example.

Examples of an alkali metal compound include alkali metal carbonate, alkali metal hydroxide, alkali metal hydride, and alkali metal alkoxide. In particular, sodium carbonate and potassium carbonate are preferred.

Examples of a dihydric phenol compound include compounds wherein hydroquinone, catechol, resorcin, 4,4'-biphenol, bis(hydroxyphenyl)alkanes (for example, 2,2-bis(hydroxyphenyl)propane and 2,2-bis(hydroxyphenyl)methane), dihydroxydiphenyl sulfones, and dihydroxydiphenyl ethers, or at least one of hydrogens of the benzene ring of these examples is substituted with a lower alkyl group such as a methyl group, an ethyl group, a propyl group or the like, or a lower alkoxy group such as a methoxy group, an ethoxy group or the like. Two or more types of the above compounds can be mixed and then used as a dihydric phenol compound.

Polyethersulfone may be a commercially available product. Examples of such a commercially available product include SUMIKAEXCEL7600P and SUMIKAEXCEL5900P (both manufactured by Sumitomo Chemical Company, Limited).

Polyethersulfone has a logarithmic viscosity of, from the viewpoint of successfully forming macrovoids of the porous polyethersulfone film, preferably 0.5 or more, and more preferably 0.55 or more, from the viewpoint of production easiness for the porous polyethersulfone film, preferably 1.0 or less, more preferably 0.9 or less, further preferably 0.8 or less, and particularly preferably 0.75 or less.

Furthermore, the porous polyethersulfone film or polyethersulfone as a raw material thereof has, from the viewpoint of heat resistance and dimensional stability under high temperatures, a glass transition temperature of 200° C. or higher, or no clear glass transition temperature is preferably observed.

<Production of Porous Polyethersulfone Film>

A porous polyethersulfone film having the above-described structure can be produced by the following method, for example. Therefore, another aspect of the present invention is to provide a method for manufacturing the above porous polyethersulfone film according to one aspect of the present invention, wherein the method comprises:

a step of flow-casting a polyethersulfone solution containing 0.3% by mass to 60% by mass of polyethersulfone having a logarithmic viscosity of 0.5 to 1.0 and 40% by mass to 99.7% by mass of an organic polar solvent to form a film, and then dipping and bringing the film into contact with a coagulating solvent containing a poor solvent or nonsolvent of polyethersulfone as an essential component, to fabricate the coagulated film having vacancies; and a step of heat treating the coagulated film having vacancies obtained in the step, and then coarsening the vacancies to obtain a porous polyethersulfone film.

The present inventors have discovered that upon production of the porous polyethersulfone film, the use of relatively a high molecular weight of polyethersulfone as a raw material is useful for producing the porous polyethersulfone film with successfully formed macrovoids. Hereafter, suitable examples of a method for manufacturing the porous polyethersulfone film are more specifically described.

(Flow Casting)

First, a polyethersulfone solution is flow-cast to form a film. The polyethersulfone solution contains preferably 0.3% by mass to 60% by mass of polyethersulfone and 40% by mass to 99.7% by mass of an organic polar solvent, more preferably 1.0% by mass to 30% by mass of polyethersulfone and 70% by mass to 99% by mass of an organic polar solvent, and further preferably 5% by mass to 15% by mass of polyethersulfone and 85% by mass to 95% by mass of an organic polar solvent.

The organic polar solvent can be selected from solvents in which polyethersulfone can be dissolved, and examples thereof include N-methyl-2-pyrrolidone (NMP), dimethyl sulfoxide, N,N-dimethylformamide, and N,N-dimethylacetamide. In view of successful formation of macrovoids, N-methyl-2-pyrrolidone is preferable.

A flow casting method is not particularly limited. For example, a polyethersulfone solution is used as a dope, the polyethersulfone solution is flow-cast onto a glass plate, a stainless plate or the like to form a film using a blade, T-die, or the like. Further, the polyethersulfone solution is intermittently or successively flow-cast onto a continuous movable belt to form a film, so that individual pieces of or a long flow-cast product can be successively produced. Such a belt may be any belt as long as it is not affected by the polyethersulfone solution and the coagulating solvent, and a belt made of metal such as stainless steel or a belt made of a resin such as polytetrafluoroethylene can be used. Moreover, the polyethersulfone solution shaped into a film through the use of T-die can be directly introduced into a coagulation bath. Furthermore, a single surface or both surfaces of a flow-cast product may be brought into contact with gasses (e.g., air and an inert gas) containing water vapor and the like, as necessary.

(Fabrication of Coagulated Film Having Vacancies)

Next, the flow-cast product is dipped or brought into contact with a coagulating solvent containing a poor solvent or nonsolvent of polyethersulfone as an essential component, polyethersulfone is precipitated to make the resultant porous, and thus a coagulated film having vacancies is fabricated. The thus obtained coagulated film having vacancies is washed and/or dried as necessary.

A poor solvent or nonsolvent of polyethersulfone is preferably water. The content of water in a coagulating solvent is preferably 20% by mass to 100% by mass, more preferably 20% by mass and 80% by mass, further preferably 30% by mass and 70% by mass, and particularly preferably 40% by mass and 60% by mass. From the viewpoint of successfully forming macrovoids, a coagulating solvent containing water and an organic polar solvent is preferably used. Examples of an organic polar solvent include N-methyl-2-pyrrolidone (NMP), dimethyl sulfoxide, N,N-dimethylformamide, and N,N-dimethylacetamide. A particularly preferable organic polar solvent is N-methyl-2-pyrrolidone. When a coagulating solvent is a mixture of water and an organic polar solvent, the contents of water and an organic polar solvent in 100% by mass of the coagulating solvent are, preferably 20% by mass to 80% by mass of water and 20% by mass to 80% by mass of the organic polar solvent, more preferably 30% by mass to 70% by mass of water and 30% by mass to 70% by mass of the organic polar solvent, and further preferably 40% by mass to 60% by mass of water and 40% by mass to 60% by mass of the organic polar solvent.

The temperature of a coagulating solvent may be selected as appropriate depending on purposes, and is, for example, −30° C. to 70° C., preferably 0° C. to 60° C., and further preferably 10° C. to 50° C.

Subsequently, the porous polyethersulfone film is obtained by heat treating the above-obtained coagulated film having vacancies, and then coarsening the vacancies of particularly the surface layer (specifically, increasing the size of vacancies). Heat treatment involves heating a coagulated film having vacancies, within a temperature region of 80° C. or higher, at a heating rate of preferably at least 10° C. and more preferably 30° C./min or more, more preferably 40° C./min or more, further preferably 50° C./min or more, particularly preferably 100° C./min or more. These heating rates are advantageous in successful coarsening of vacancies. The heating rate can be, from the viewpoint of stable formation of macrovoids in a desired shape, preferably 300° C./min or less, and more preferably 270° C./min or less.

With regard to successful coarsening of vacancies, the temperature is increased to preferably the glass transition temperature or higher of polyethersulfone, or preferably 240° C. or higher, or 250° C. or higher, or 260° C. or higher.

In the meantime, from the viewpoint of preventing the decomposition of polyethersulfone during heat treatment, the temperature is increased to preferably 350° C. or lower, or 300° C. or lower.

In the porous polyethersulfone film, porosity, film thickness, average pore diameter, and maximum pore diameter, etc., can be adjusted through appropriate selection of a polymer type, the polymer concentration in a polymer solution, viscosity and solvent species, coagulation conditions (e.g., control of solvent substitution rate, temperature, and coagulating solvent species), and the like to be employed.

In the porous polyethersulfone film, the surface treatment of the film may be performed by performing corona discharge treatment, plasma discharge treatment such as low-temperature plasma discharge or atmospheric plasma discharge, chemical etching or the like for at least a single surface thereof according to the purpose, for example. Moreover, the surface layer (a) and/or (b) may be subjected to facing and then used. The material permeability, surface pore diameter, and wettability of the film can be controlled by these treatments.

EXAMPLES

Hereafter, the present invention will be more specifically described with reference to Examples, but the present invention is not limited to these Examples.
(Evaluation of Porous Polyethersulfone Film)
1) Film Thickness
A film thickness was measured using a contact type thickness meter.
2) Gas Permeability
Gurley value (number of seconds required for 100 cc of air to pass through the film under pressure of 0.879 g/m$^2$) was measured in accordance with JIS P8117.
3) Surface Average Pore Diameter
Based on the scanning electron micrograph of the porous film surface, the pore areas of 200 or more openings were measured. The average diameter was found by calculation of the average value of the pore areas according to the following equation assuming that the pore shape was perfect circle.

Average pore diameter=$2\times(Sa/\pi)^{0.5}$ (in the equation, Sa denotes the average value of pore areas.)
4) Surface Maximum Pore Diameter
Based on the scanning electron micrograph of a surface of the porous polyethersulfone film, the pore areas of 200 or more openings were measured. Diameters were calculated from the pore areas assuming that the shape of pores is perfect circle, determining the maximum value as the maximum pore diameter.
5) Average Pore Diameter of Macrovoids in the Film Plane Direction
The pore diameters of 5 or more pores in a cross section of a scanning electron micrograph were measured, the values were averaged to find an average pore diameter.
6) Porosity
The porous polyethersulfone film was cut into pieces having a predetermined size, the film thickness and mass were measured, and then porosity was found by the following equation with a basis mass.

Porosity=$(1-(w/(S\times d\times D))\times 100(\%)$ (in the equation, S denotes the area of a film, d denotes a film thickness, w denotes measured mass, and D denotes the density of polyethersulfone. The density of polyethersulfone is designated as 1.37 g/cm$^3$.)

7) Glass Transition Temperature (° C.)
Dynamic viscoelasticity measurement was performed using a solid viscoelasticity analyzer under conditions of tensile mode, frequency of 10 Hz, distortion of 2%, and nitrogen gas atmosphere. In the temperature dispersion profile, a temperature at which the loss tangent reached the maximum value was designated as a glass transition temperature.
8) Logarithmic Viscosity
The logarithmic viscosity of polyethersulfone was calculated from the relative viscosity of a dilute solution in 0.5 g/dL N-methyl-2-pyrrolidone. The relative viscosity was measured using Ubbelohde viscometer.
9) Mean Flow Pore Diameter
Mean flow pore diameter was measured using a palm porometer (POROMETER 3G zh (Quantachrome Instruments)).

Preparation Example 1

(Preparation of Polyethersulfone Solution (A))
Polyethersulfone (SUMIKAEXCEL7600P: Sumitomo Chemical Company, Limited, logarithmic viscosity: 0.701) was weighed and then added into a 500-ml separable flask using N-methyl-2-pyrrolidone (NMP) as a solvent in such a manner that the polymer concentration was 10% by mass. Subsequently, the flask was covered with a separable cover fitted with a stirring blade, a nitrogen introducing pipe, and an exhaust pipe, and then the solution was stirred for 24 hours while keeping the temperature at 50° C. with the use of an oil bath, so that a viscous and clear liquid, polyethersulfone solution (A), was obtained.

Preparation Example 2

(Preparation of Polyethersulfone Solution (B))
The same operation as in Preparation Example 1 was performed except for using SUMIKAEXCEL5900P (Sumitomo Chemical Company, Limited, logarithmic viscosity: 0.596) as polyethersulfone, so that a viscous and clear liquid, polyethersulfone solution (B) was obtained.

Preparation Example 3

(Preparation of Polyethersulfone Solution (C))
The same operation as in Preparation Example 1 was performed except for using SUMIKAEXCEL4100P (Sumitomo Chemical Company, Limited, logarithmic viscosity: 0.422) as polyethersulfone, so that a viscous and clear liquid, polyethersulfone solution (C) was obtained.

Examples 1 to 12

A 20 cm-square stainless substrate with a mirror-polished surface was coated uniformly with polyethersulfone solution (A) or (B) prepared in Preparation Example 1 by flow casting at room temperature using a tabletop automatic coater in such a manner that the thickness was about 100 μm to 300 μm. Subsequently, the solution was left to stand for 90 seconds in air at a temperature of 23° C. and with humidity of 40%, and then the substrate was entirely placed into a mixed coagulation bath containing an aqueous solution having an NMP concentration (% by mass) depicted in Table 1. After placement, the substrate was left to stand for 10 minutes, so as to precipitate a polyethersulfone film on the substrate. Thereafter, the substrate was removed from the bath, the polyethersulfone film precipitated on the substrate was peeled off, and then dipped in pure water for 5 minutes, thereby obtaining a polyethersulfone film. The polyethersulfone film was dried in air at a temperature of 23° C. and with humidity of 40%, fitted to a 10 cm-square pin tenter, and then set in an electric furnace. This was heated up to 80° C. at a heating rate of about 10° C./min, heated to a temperature depicted in Table 1 at a heating rate depicted in Table 1, and then kept as such for 3 minutes. Heat treatment was performed according to this temperature profile, thereby obtaining a porous polyethersulfone film. The properties of the obtained film are depicted in Table 1 and Table 2.

The cross section of the porous polyethersulfone film was observed with a scanning electron microscope, so that a large number of macrovoids having a length in the film lateral direction of 10 μm or more could be confirmed. For example, the porous polyethersulfone film of example 2 was confirmed as follows:

Of the voids having a length in the lateral direction of 5 μm or more, the number of voids, of which the ratio L/d of the length in the lateral direction (L) to the length in the film thickness direction (d) fell within a range of from L/d=0.5 to 3, was at least 60%; and The film had a large number of macrovoids having a length in the film lateral direction of at least 10 μm, and the cross-sectional area of macrovoids having an average pore diameter in the film plane direction of 10 μm to 500 μm accounted for 60% or more of the overall cross-sectional area of the film. Measurement results are partially depicted in Table 1 and Table 2.

The glass transition temperature of the porous polyethersulfone film was about 240° C. (in examples using polyethersulfone solutions (A) and (B)).

Moreover, the surface of the porous polyethersulfone film was observed with a scanning electron microscope, confirming that the porous structure had a large number of through-pores running toward the surface on the substrate side of the film.

Examples A to E

A porous polyethersulfone film was obtained in the same manner as in Example 1 except for using polyethersulfone solution (C) instead of polyethersulfone solution (A). Properties of the thus obtained porous polyethersulfone film are depicted in Table 3.

The surface of the porous polyethersulfone film obtained in Example A was observed with a scanning electron microscope, confirming that the two surface layers had almost no opening.

Example F

The same operation as in Example 1 was performed except for using a mixed coagulation bath containing an aqueous solution with an NMP concentration of 80% by mass, thereby obtaining a porous polyethersulfone film. Properties of the thus obtained film are depicted in Table 3.

The surface of the porous polyethersulfone film obtained in Example F was observed with a scanning electron microscope, confirming that the two surface layers had almost no opening.

Figure 2:
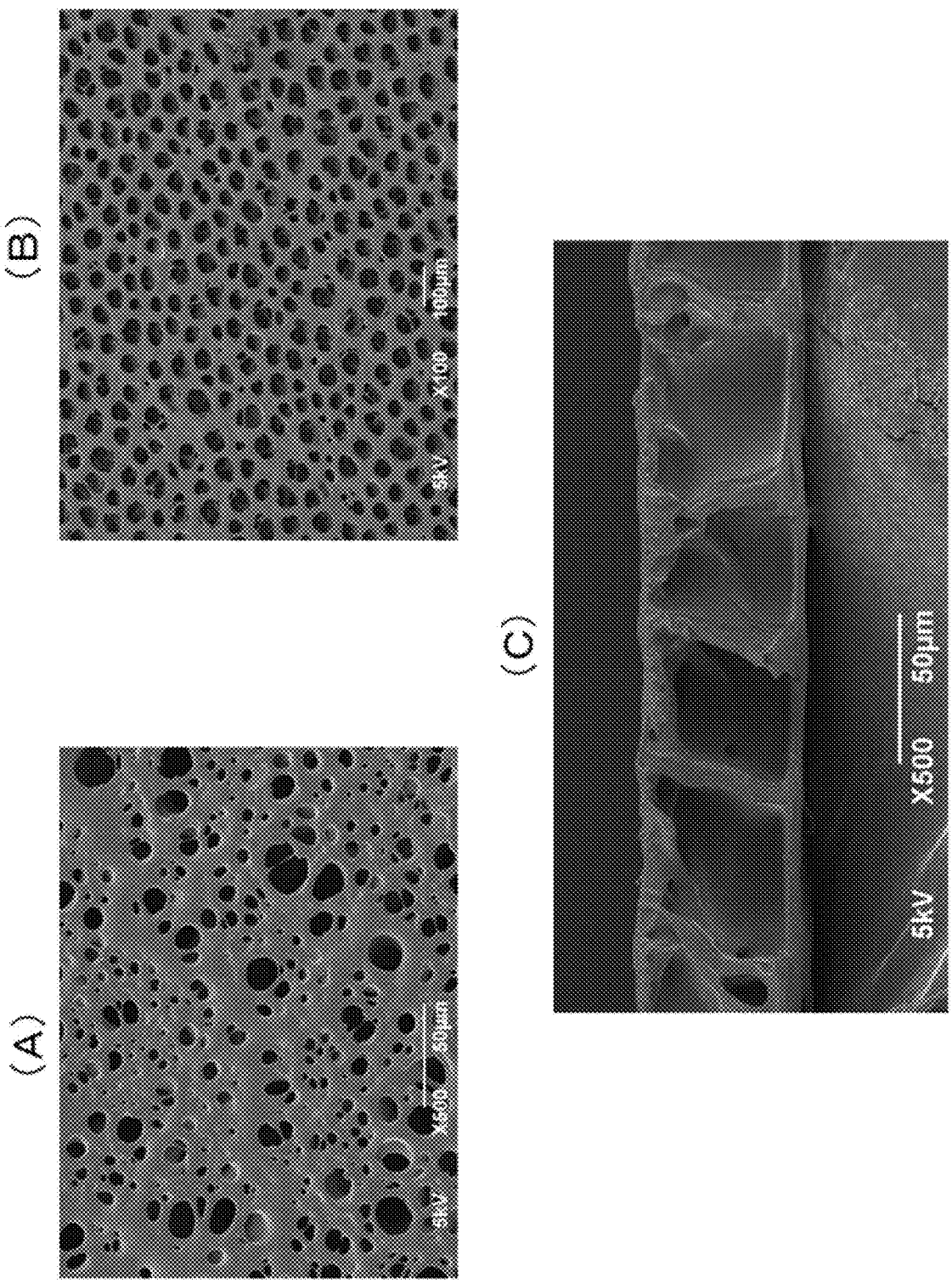
FIG. 2 illustrates scanning electron micrographs of the porous polyethersulfone film obtained in Example 4, wherein (A) depicts the surface on the side of the surface layer (a), (B) depicts the surface on the side of the surface layer (b), and (C) depicts a cross section (the upper side of the page denotes the side of the surface layer (a), and the lower side of the page denotes the side of the surface layer (b).).

FIG. 1 illustrates scanning electron micrographs of the porous polyethersulfone film obtained in Example 2. FIG. 2 illustrates scanning electron micrographs of the porous polyethersulfone film obtained in Example 4. In FIG. 1 and FIG. 2, (A) depicts the surface on the side of the surface layer (a), (B) depicts the surface on the side of the surface layer (b), and (C) is a cross section (the upper side of the page denotes the side of the surface layer (a), and the lower side of the page denotes the side of the surface layer (b)).

TABLE 1

| | | NMP concentration of coagulating bath (mass %) | Original film properties | | | Heat treatment conditions | | Porous film properties | | |
|---|---|---|---|---|---|---|---|---|---|---|
| | Raw-material solution | | Thickness (μm) | Porosity (%) | Gurley value (sec/100 cc) | Heating rate (° C./min) | Maximum temperature (° C.) | Thickness (μm) | Porosity (%) | Gurley value (sec/100 cc) |
| Example 1 | A | 20 | 77 | 88 | 14 | 10 | 270 | 37 | 76 | 0.1 |
| Example 2 | A | 40 | 30 | 67 | 18 | 10 | 270 | 25 | 60 | 0.1 |
| Example 3 | A | 40 | 60 | 85 | 11 | 10 | 260 | 36 | 76 | 0.6 |
| Example 4 | A | 40 | 80 | 76 | 23 | 10 | 270 | 54 | 64 | 0.2 |
| Example 5 | A | 40 | 60 | 85 | 11 | 140 | 280 | 35 | 74 | 0.1 |
| Example 6 | A | 40 | 60 | 85 | 11 | 267 | 245 | 40 | 78 | 0.5 |
| Example 7 | A | 40 | 60 | 85 | 11 | 267 | 315 | 31 | 72 | 0.1 |
| Example 8 | A | 60 | 58 | 86 | 12 | 10 | 270 | 41 | 80 | 0.1 |
| Example 9 | A | 60 | 97 | 88 | 21 | 10 | 270 | 81 | 79 | 0.3 |
| Example 10 | B | 0 | 100 | 90 | 29 | 10 | 270 | 33 | 72 | 0.1 |
| Example 11 | B | 20 | 97 | 88 | 32 | 10 | 270 | 41 | 73 | 0.1 |
| Example 12 | B | 40 | 91 | 86 | 114 | 10 | 270 | 32 | 66 | 0.1 |

TABLE 2

| | Surface A | | Surface B | | Average pore diameter in the plane direction of macrovoid [μm] | Mean flow pore diameter [μm] |
|---|---|---|---|---|---|---|
| | Average surface opening ratio [%] | Average surface opening diameter [μm] | Average surface opening ratio [%] | Average surface opening diameter [μm] | | |
| Example 1 | 23 | 14 | 34 | 30 | 19 | 15 |
| Example 3 | 19 | 12 | 36 | 32 | 21 | 14 |

TABLE 2-continued

| | Surface A | | Surface B | | Average pore diameter in the plane direction of macrovoid [μm] | Mean flow pore diameter [μm] |
|---|---|---|---|---|---|---|
| | Average surface opening ratio [%] | Average surface opening diameter [μm] | Average surface opening ratio [%] | Average surface opening diameter [μm] | | |
| Example 6 | 21 | 15 | 33 | 49 | 36 | 18 |
| Example 8 | 19 | 14 | 21 | 47 | 49 | 16 |

TABLE 3

| | NMP | Original film properties | | | Heat treatment conditions | | Porous film properties | | |
|---|---|---|---|---|---|---|---|---|---|
| | Raw-material solution | concentration of coagulating bath(mass %) | Thickness (μm) | Porosity (%) | Gurley value (sec/100 cc) | Heating rate (° C./min) | Maximum temperature (° C.) | Thickness (μm) | Porosity (%) | Gurley value (sec/100 cc) |
| Example A | C | 0 | 104 | 86 | ∞ | 10 | 270 | 73 | 67 | ∞ |
| Example B | C | 20 | 97 | 88 | 482 | 10 | 270 | 69 | 64 | 320 |
| Example C | C | 40 | 91 | 86 | 455 | 10 | 270 | 55 | 59 | 263 |
| Example D | C | 60 | 72 | 86 | 397 | 10 | 270 | 45 | 60 | 101 |
| Example E | C | 80 | 57 | 63 | 1830 | 10 | 270 | 31 | 47 | 1030 |
| Example F | A | 80 | 46 | 82 | ∞ | 10 | 270 | 11 | 22 | ∞ |

INDUSTRIAL APPLICABILITY

The porous polyethersulfone film of the present invention can be suitably used for applications including material separation films (for example, a liquid filtering membrane and a gas separation membrane etc.), insulating materials, and cell culture sheets, for example.

The invention claimed is:

1. A porous polyethersulfone film having a surface layer (a), a surface layer (b), and a macrovoid layer sandwiched between the surface layer (a) and the surface layer (b),
    wherein the macrovoid layer has a partition wall bonded to the surface layers (a) and (b); and a plurality of macrovoids surrounded by the partition wall and the surface layers (a) and (b), the macrovoids having an average pore diameter in a film plane direction of 10 μm to 500 μm;
    wherein the partition wall of the macrovoid layer has a thickness of 0.1 μm to 50 μm;
    wherein each of the surface layers (a) and (b) has a thickness of 0.1 μm to 50 μm;
    wherein one of the surface layers (a) and (b) has a plurality of fine pores having an average pore diameter of more than 5 μm and not more than 200 μm, while the other has a plurality of fine pores having an average pore diameter of not less than 0.01 μm and not more than 200 μm;
    wherein a surface opening ratio of one of the surface layers (a) and (b) is not less than 15%, while the surface opening ratio of the other surface layer is not less than 10%;
    wherein the fine pores in the surface layers (a) and (b) communicate with the plurality of macrovoids; and
    wherein the porous polyethersulfone film has a total film thickness of 5 μm to 500 μm, and a porosity of 50% to 95%.

2. The porous polyethersulfone film according to claim 1, wherein a mean flow pore diameter measured by a palm porometer is 5 to 200 μm.

3. The porous polyethersulfone film according to claim 1, wherein the partition wall of the macrovoid layer, and the surface layers (a) and (b) have generally the same thickness.

4. The porous polyethersulfone film according to claim 1, wherein a Gurley value is not more than 20 secs.

5. The porous polyethersulfone film according to claim 1, wherein in a cross section of the porous polyethersulfone film cut perpendicularly to the film plane direction, a cross-sectional area of the macrovoid having an average pore diameter in the film plane direction of 10 μm to 500 μm is not less than 50% of a film cross-sectional area.

6. The porous polyethersulfone film according to claim 1, wherein in a cross section of the porous polyethersulfone film cut perpendicularly to the film plane direction, not less than 60% of a total number of the macrovoids has a ratio (L/d) of 0.5 to 3 of a length (L) in the film plane direction to a length (d) in the film thickness direction.

7. The porous polyethersulfone film according to claim 1, wherein a glass transition temperature of the porous polyethersulfone film is 200° C. or higher, or a clear transition temperature of the porous polyethersulfone film is not observed.

8. The method for manufacturing a porous polyethersulfone film according to claim 1, the method comprising the steps of:
    casting a polyethersulfone solution (A) containing 0.3% by mass to 60% by mass of a polyethersulfone having a logarithmic viscosity of 0.5 to 1.0, and 40% by mass to 99.7% by mass of an organic polar solvent in a film shape, and dipping or bringing into contact with a coagulating solvent containing a nonsolvent of polyethersulfone as an essential component to fabricate a coagulated film having a vacancy; and
    performing a heat treatment of the coagulated film having a vacancy obtained in the step to coarsen the vacancy to obtain a porous polyethersulfone film;
    wherein the heat treatment comprises heating up the coagulated film having the vacancy to a glass transition temperature of the polyethersulfone or higher, or to 240° C. or higher.

9. The method for manufacturing a porous polyethersulfone film according to claim 8, wherein the heat treatment is performed at a heating rate of 10° C./min or higher in a temperature region of 80° C. or higher.

10. The method for manufacturing a porous polyethersulfone film according to claim 1,
the method comprising the steps of:
casting a polyethersulfone solution (A) containing 0.3% by mass to 60% by mass of a polyethersulfone having a logarithmic viscosity of 0.5 to 1.0, and 40% by mass to 99.7% by mass of an organic polar solvent in a film shape, and dipping or bringing into contact with a coagulating solvent containing water as an essential component to fabricate a coagulated film having a vacancy; and
performing a heat treatment of the coagulated film having a vacancy obtained in the step to coarsen the vacancy to obtain a porous polyethersulfone film;
wherein the heat treatment comprises heating up the coagulated film having the vacancy to a glass transition temperature of the polyethersulfone or higher, or to 240° C. or higher.

11. The method for manufacturing a porous polyethersulfone film according to claim 10, wherein a ratio of water in the coagulating solvent is 20% by mass to 100% by mass.

* * * * *